(12) United States Patent
Alvarez et al.

(10) Patent No.: US 10,435,585 B2
(45) Date of Patent: Oct. 8, 2019

(54) CURABLE COMPOSITION, METHOD OF PREPARING CURED ARTICLE, AND CURED ARTICLE FORMED THEREBY

(71) Applicant: Dow Corning Corporation, Midland, MI (US)

(72) Inventors: Khristopher Alvarez, Midland, MI (US); Chad Amb, Hudson, WI (US); Sarah Breed, Muskegon, MI (US); Brandon Swatowski, Sanford, MI (US)

(73) Assignee: Dow Corning Corporation, Midland, MI (US)

( * ) Notice: Subject to any disclaimer, the term of this patent is extended or adjusted under 35 U.S.C. 154(b) by 143 days.

(21) Appl. No.: 14/890,707

(22) PCT Filed: May 15, 2014

(86) PCT No.: PCT/US2014/038083
§ 371 (c)(1),
(2) Date: Nov. 12, 2015

(87) PCT Pub. No.: WO2014/186514
PCT Pub. Date: Nov. 20, 2014

(65) Prior Publication Data
US 2016/0102226 A1 Apr. 14, 2016

Related U.S. Application Data

(60) Provisional application No. 61/824,424, filed on May 17, 2013.

(51) Int. Cl.
| | | |
|---|---|---|
| *C09D 183/06* | (2006.01) | |
| *C07F 7/08* | (2006.01) | |
| *B05D 3/02* | (2006.01) | |
| *B05D 7/04* | (2006.01) | |
| *B05D 7/00* | (2006.01) | |
| *C08J 7/04* | (2006.01) | |
| *G02B 1/04* | (2006.01) | |
| *G02B 6/138* | (2006.01) | |

(52) U.S. Cl.
CPC ......... *C09D 183/06* (2013.01); *B05D 3/0254* (2013.01); *B05D 7/04* (2013.01); *B05D 7/584* (2013.01); *C07F 7/081* (2013.01); *C07F 7/0812* (2013.01); *C08J 7/047* (2013.01); *G02B 1/045* (2013.01); *C08J 2379/08* (2013.01); *C08J 2483/06* (2013.01); *G02B 6/138* (2013.01)

(58) Field of Classification Search
CPC ........ B05D 3/0254; B05D 7/04; B05D 7/584; C07F 7/0812; C07F 7/0818; C08J 2379/08; C08J 2483/06; C08J 7/047; C09D 183/06; G02B 1/045; G02B 6/138
See application file for complete search history.

(56) References Cited

U.S. PATENT DOCUMENTS

| | | | |
|---|---|---|---|
| 4,082,719 A | | 4/1978 | Liles et al. |
| 5,260,455 A | * | 11/1993 | Eckberg ............... C07F 7/08 522/25 |
| 6,022,050 A | | 2/2000 | Kline |
| 6,027,672 A | | 2/2000 | Weitzel et al. |
| 6,905,904 B2 | | 6/2005 | Gardner et al. |
| 7,166,322 B2 | | 1/2007 | Inui et al. |
| 7,771,794 B2 | | 8/2010 | Watanabe et al. |
| 7,811,640 B2 | | 10/2010 | Charters et al. |
| 7,863,391 B2 | | 1/2011 | Morita et al. |
| 7,968,274 B2 | | 6/2011 | Shimizu |
| 8,211,547 B2 | | 7/2012 | Irifune et al. |
| 8,715,905 B2 | | 5/2014 | Tagami et al. |
| 8,861,916 B2 | | 10/2014 | Bahadur et al. |
| 2008/0058441 A1 | * | 3/2008 | Watanabe ............ C08L 83/06 522/170 |
| 2008/0085985 A1 | * | 4/2008 | Nakamura ........... C08L 63/00 528/25 |
| 2008/0319144 A1 | | 12/2008 | Morita et al. |
| 2009/0246540 A1 | * | 10/2009 | Irifune ................. C08G 77/14 428/447 |
| 2011/0176764 A1 | | 7/2011 | Beals et al. |
| 2013/0221400 A1 | | 8/2013 | Tanikawa et al. |

FOREIGN PATENT DOCUMENTS

| | | | |
|---|---|---|---|
| JP | 59-048942 | * | 12/1984 |
| JP | 11293114 | | 10/1999 |
| JP | 2003185862 | | 7/2003 |
| JP | 2004-352771 A | | 12/2004 |
| JP | 2006307088 | | 11/2006 |
| JP | 2011137109 | | 7/2011 |

(Continued)

OTHER PUBLICATIONS

Translation of JP 59-048942, retrieved Aug. 26, 2018.*
Chung, P. H.; Crivello, J. V.; Fan, M.; "The Use of Platinum and Rhodium Catalysts for the Preparation and Cationic Ring Opening Polymerization of Silicon-Containing Epoxides" Journal of Polymer Science: Part A Polymer Chemistry, vol. 31,1741-1746 (1993).
Zheng, Y; Chonung, K.; Jin, X.; Wei, P.; Jiang, P.; "Study on the Curing Reaction, Dielectric and Thermal Performances of Epoxy Impregnating Resin with Reactive Silicon Compounds as New Diluents" Journal of Applied Polymer Science, vol. 107, 3127-3136 (2008).

(Continued)

*Primary Examiner* — Michael B Nelson

(57) ABSTRACT

A curable composition comprises a cationic polymerizable material. The curable composition further comprises a diluent component comprising a silane compound having a single silicon-bonded cationic polymerizable group. A method of forming a cured article with the curable composition is also disclosed. The method comprises applying the curable composition on a substrate to form a film. The method further comprises curing the film on the substrate to form the cured article. The present invention also provides the cured article formed in accordance with the method.

11 Claims, No Drawings

(56) References Cited

FOREIGN PATENT DOCUMENTS

| | | |
|---|---|---|
| JP | 2008-260894 A | 1/2013 |
| WO | 2011084250 | 7/2011 |
| WO | 2014186514 A1 | 11/2014 |
| WO | 2014186549 A1 | 11/2014 |

OTHER PUBLICATIONS

JP2006307088, machine translation.
JP11293114, machine translation.
JP2011137109, machine translation.
JP2003185862, Machine translation.
Search report from corresponding European 14730038.8 application, dated Feb. 15, 2019.

* cited by examiner

CURABLE COMPOSITION, METHOD OF PREPARING CURED ARTICLE, AND CURED ARTICLE FORMED THEREBY

CROSS REFERENCE TO RELATED APPLICATIONS

This application is a U.S. national stage filing under 35 U.S.C. § 371 of PCT Application No. PCT/US14/038083 filed on 15 May 2014, currently pending, which claims the benefit of U.S. Provisional Patent Application No. 61/824,424 filed 17 May 2013 under 35 U.S.C. § 119 (e). PCT Application No. PCT/US14/038083 and U.S. Provisional Patent Application No. 61/824,424 are hereby incorporated by reference.

The present invention generally relates to a curable composition and, more specifically, to a curable composition comprising a cationic polymerizable material, a method of preparing a cured article therewith, and a cured article formed thereby.

Curable compositions are known in the art and utilized in numerous applications. One particular type of curable composition is a cationic polymerizable composition, which cures (or polymerizes) under cationic conditions, often initiated by active energy rays. Such cationic polymerizable compositions are utilized in various applications where curing solely with heat is undesirable.

For example, cationic polymerizable compositions are often utilized to fabricate optical articles and elements, e.g. waveguides. Initially, waveguides were rigid with a high modulus, and thus the cationic polymerizable compositions cured to have a very high cross-link density. However, flexible waveguides are increasingly desirable, in which case the flexible waveguides are prepared on a flexible substrate, such as polyimide. However, use of such flexible substrates gives rise to a host of new issues, such as curling and separation of a cured layer and the flexible substrate. This is generally attributable to differences in the coefficient of thermal expansion of the flexible substrate and the cured layer.

SUMMARY OF THE INVENTION

The present invention provides a curable composition. The curable composition comprises a cationic polymerizable material. The curable composition further comprises a diluent component comprising a silane compound having a single silicon-bonded cationic polymerizable group.

The present invention also provides a method of preparing a cured article. The method comprises applying the curable composition on a substrate to form a film. The method further comprises curing the film on the substrate to form the cured article. The present invention also provides the cured article formed in accordance with the method.

The curable composition of the present invention may be utilized to form cured articles having excellent physical properties, including a selectively-controlled refractive index, as well as hardness and elasticity without deformation, buckling, or formation of cracks. Further, the cured article has excellent physical properties and is generally free from curling or warping.

DETAILED DESCRIPTION OF THE INVENTION

The present invention provides a curable composition. The curable composition may be utilized to form cured articles having excellent physical properties, which makes the cured articles suitable for use in numerous different applications, as described in greater detail below.

The curable composition comprises a cationic polymerizable material. The cationic polymerizable material may comprise any material that is capable of cationic polymerization. For example, the cationic polymerizable material may be organic, inorganic, or combinations thereof. Further, the cationic polymerizable material may comprise monomers, oligomers, polymers, resins, and combinations thereof.

Independent of the type of cationic polymerizable material utilized in the curable composition, the cationic polymerizable material includes at least one cationic polymerizable group. Cationic polymerizable materials are typically curable upon exposure to active-energy rays via a cationic reaction mechanism. The cationic polymerizable group may be a neutral group or moiety. That is, the term "cationic" modifies polymerizable rather than group. The cationic polymerizable group may be located at any position(s) of the cationic polymerizable material. For example, the cationic polymerizable group may be pendent from or a substituent of the cationic polymerizable compound. The at least one cationic polymerizable group is referred to herein merely as "the cationic polymerizable group," which, although singular, encompasses embodiments in which the cationic polymerizable group includes more than one cationic polymerizable group, i.e., two or more cationic polymerizable groups. Typically, the cationic polymerizable material includes two or more cationic polymerizable groups, which are independently selected.

In certain embodiments, the cationic polymerizable group comprises a heterocyclic functional group, defined as a cyclic organic functional group including at least one heteroatom, such as S, N, O, and/or P; alternatively S, N, and/or O. For example, heterocyclic groups include, but are not limited to, lactone groups, lactam groups, cyclic ethers, and cyclic amines. Lactone groups are generally cyclic esters and may be selected from, for example, an acetolactone, a propiolactone, a butyrolactone, and a valerolactone. Lactam groups are generally cyclic amides and may be selected from, for example, a β-lactam, a γ-lactam, a δ-lactam and an ε-lactam. Specific examples of cyclic ethers include oxirane, oxetane, tetrahydrofuran, and dioxepane (e.g. 1,3-dioxepane). Additional examples of heterocyclic functional groups include thietane and oxazoline. Notably, the heterocyclic functional groups described above may also exist as monomers. However, in the context of the cationic polymerizable group, the heterocyclic functional groups set forth above are substituents of a larger molecule and not discrete monomers. Further, these groups may be bonded or connected to the cationic polymerizable material via a divalent linking group.

In other embodiments, the cationic polymerizable group may comprise a cationic polymerizable group other than a heterocyclic functional group. For example, the cationic polymerizable group may alternatively be selected from an ethylenically unsaturated group, such as a vinyl, a vinyl ether, a divinyl ether, a vinyl ester, a diene, a tertiary vinyl, a styrene, or a styrene-derivative group.

Combinations of different heterocyclic functional groups, or combinations of cationic polymerizable groups other than heterocyclic functional groups, or combinations of heterocyclic functional groups and cationic polymerizable groups other than heterocyclic functional groups, may be included in the cationic polymerizable material.

In certain embodiments, the cationic polymerizable group is selected from a cyclic ether, a cyclic ester, a thietane, a dioxepane, a cyclic carbonate, a vinyl ether, a divinyl ether, a vinyl ester, a diene, a tertiary vinyl, a styrene, and a styrene-derivative group. Typically, the cationic polymerizable group is a heterocyclic functional group. Most typically, the heterocyclic functional group is a cyclic ether, e.g. oxirane, which is also known as epoxide. Epoxide-functional materials are often colloquially referred to as epoxy-functional materials.

In certain embodiments in which the cationic polymerizable material is organic, the cationic polymerizable material comprises an olefinic or polyolefinic material. In other embodiments, the organic cationic polymerizable material comprises an organic epoxy-functional material, such as an epoxy resin. Specific examples of epoxy resins include bisphenol-type epoxy resins, such as bisphenol-A type, bisphenol-F type, bisphenol-AD type, bisphenol-S type, and hydrogenated bisphenol-A type epoxy resin; a naphthalene-type epoxy resin; a phenol-novolac-type epoxy resin; a biphenyl-type epoxy resin; a glycidylamine-type epoxy resin; an alicyclic-type epoxy resin; or a dicyclopentadiene-type epoxy resin. These epoxy resins can be used in combinations of two or more as the cationic polymerizable material of the curable composition. Alternatively still, the organic cationic polymerizable material may comprise a polyacrylic, a polyamide, a polyester, etc. or other organic polymeric material including the cationic polymerizable group. "Organic material," as used herein, is distinguished from a silicone material, with silicone materials having a backbone comprising siloxane bonds (Si—O—Si) and organic materials having a carbon-based backbone and lacking siloxane bonds.

In other embodiments, the cationic polymerizable material comprises a silicone material. The silicone material generally comprises organosiloxane macromolecules, wherein each macromolecule independently may be straight or branched. The silicone material may be any silicone material so long as the silicone material is capable of cationic polymerization. By silicone material, it is meant that the silicone material includes at least one siloxane bond, i.e., an Si—O—Si bond. For example, the silicone material may comprise a solid silicone, a liquid silicone, a dispersion of a silicone, a mixture of a silicone with an organic and/or inorganic compound, or a combination thereof. More specifically, the silicone material may be in the form of liquid, fluid, gum, gel, solid, resin, rubber, grease, or combinations thereof, either in a cured or uncured state. The silicone material may be crosslinked or not crosslinked and may be cured or uncured. If cured, however, the silicone material is still capable of undergoing cationic polymerization, i.e., the silicone material still includes the cationic polymerizable group, even if otherwise cross-linked or cured.

The silicone material may comprise any combination of siloxane units, i.e., the silicone material comprise any combination of $R_3SiO_{1/2}$ units, i.e., M units, $R_2SiO_{2/2}$ units, i.e., D units, $RSiO_{3/2}$ units, i.e., T units, and $SiO_{4/2}$ units, i.e., Q units, where R is typically independently selected from a substituted or unsubstituted hydrocarbyl group or cationic polymerizable group. For example, R may be aliphatic, aromatic, cyclic, alicyclic, etc. Further, R may include ethylenic unsaturation. By "substituted," it is meant that one or more hydrogen atoms of the hydrocarbyl may be replaced with atoms other than hydrogen (e.g. a halogen atom, such as chlorine, fluorine, bromine, etc.), or a carbon atom within the chain of R may be replaced with an atom other than carbon, i.e., R may include one or more heteroatoms within the chain, such as oxygen, sulfur, nitrogen, etc. R typically has from 1 to 10 carbon atoms. For example, R may have from 1 to 6 carbon atoms when aliphatic, or from 6 to 10 carbon atoms when aromatic. Substituted or unsubstituted hydrocarbyl groups containing at least 3 carbon atoms can have a branched or unbranched structure. Examples of hydrocarbyl groups represented by R include, but are not limited to, alkyl, such as methyl, ethyl, propyl, butyl, hexyl, heptyl, octyl, nonyl, decyl, and isomers of such groups; alkenyl, such as vinyl, allyl, and hexenyl; cycloalkyl, such as cyclopentyl, cyclohexyl, and methylcyclohexyl; aryl, such as phenyl and naphthyl; alkaryl, such as tolyl and xylyl; and aralkyl, such as benzyl and phenethyl. Examples of halogen-substituted hydrocarbyl groups represented by R are exemplified by 3,3,3-trifluoropropyl, 3-chloropropyl, chlorophenyl, dichlorophenyl, 2,2,2-trifluoroethyl, 2,2,3,3-tetrafluoropropyl, and 2,2,3,3,4,4,5,5-octafluoropentyl. Examples of the cationic polymerizable group represented by R are set forth above.

When the silicone material comprises a rubber, elastomer, or gel, the silicone material comprises or is formed from at least one polymer including repeating D units, i.e., a linear or partly branched polymer. Alternatively, when the silicone material is resinous, the silicone material generally includes a silicone resin having T and/or Q units. The cationic polymerizable group(s) may be present in any of the M, D, and/or T units of the silicone material.

In embodiments in which the silicone material is resinous, the silicone material may comprise a DT resin, an MT resin, an MDT resin, a DTQ resin, an MTQ resin, an MDTQ resin, a DQ resin, an MQ resin, a DTQ resin, an MTQ resin, or an MDQ resin. Combinations of different resins may be present in the silicone material. Moreover, the silicone material may comprise a resin in combination with a polymer.

In one specific embodiment, the silicone material comprises or consists of an organopolysiloxane resin. The organopolysiloxane resin may be represented by the following siloxane unit formula:

where $R^1$, $R^2$, $R^3$, $R^4$, $R^5$, and $R^6$ are independently selected from R, which is defined above; a+b+c+d=1; "a" on average satisfies the following condition: $0 \leq a < 0.4$; "b" on average satisfies the following condition: $0 < b < 1$; "c" on average satisfies the following condition: $0 < c < 1$; "d" on average satisfies the following condition; $0 \leq d < 0.4$; and "b" and "c" are typically bound by the following condition: $0.01 \leq b/c \leq 3$. Subscripts a, b, c, and d designate an average mole number of each siloxane unit. Said differently, these subscripts represent an average mole % or share of each siloxane unit in one molecule of the organopolysiloxane resin. Because $R^{1-6}$ are independently selected from R, the siloxane unit formula above can be rewritten as follows:

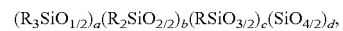

where R is independently selected and defined above, and a-d are defined above.

Typically, in one molecule of the organopolysiloxane resin, siloxane units including a cationic polymerizable group constitute 2 to 50 mole % of total siloxane units. Further, in these embodiments, at least 15 mole % of all silicon-bonded organic groups comprise univalent aromatic hydrocarbon groups with 6 to 10 carbon atoms (e.g. aryl groups).

The organopolysiloxane resin contains $(R^4R^5SiO_{2/2})$ and $(R^6SiO_{3/2})$ as indispensable units. However, the organopolysiloxane may additionally comprise structural units ($R^1R^2R^3SiO_{1/2}$) and ($SiO_{4/2}$). In other words, the epoxy-containing organopolysiloxane resin may be composed of the units shown in the following formulae:

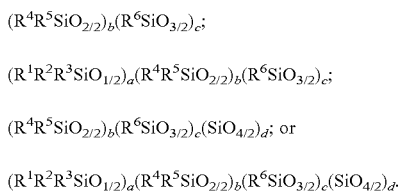

If the content of the ($R^1R^2R^3SiO_{1/2}$) units is too high, the molecular weight of the organopolysiloxane resin is reduced, and the following condition takes place: $0 \le a < 0.4$. If ($SiO_{4/2}$) units are introduced under this condition, a cured product of the organopolysiloxane resin may become undesirably hard and brittle. Therefore, in certain embodiments, the following condition is met: $0 \le d < 0.4$; alternatively $0 \le d < 0.2$; alternatively $d=0$. The mole ratio b/c of the indispensable structural units ($R^4R^5SiO_{2/2}$) and ($R^6SiO_{3/2}$) should be from 0.01 to 0.3, alternatively from 0.01 to 0.25, alternatively from 0.02 to 0.25. Beyond these limits, the preparation of the organopolysiloxane resin may be accompanied by the formation of insoluble by-products, or the cured product obtained by curing the curable composition will be subject to decrease in toughness and the generation of cracks, as well as to significant decrease in strength and elasticity. Because the organopolysiloxane resin contains ($R^4R^5SiO_{2/2}$) and ($R^6SiO_{3/2}$) as indispensable units, the molecular structure may vary mainly between branched, net-like and three-dimensional.

The refractive index of the organopolysiloxane resin, and of the cured product formed therefrom, may be modified. This may be particularly desirable based on the applications or end uses in which the cured product is utilized. To this end, the refractive index of the organopolysiloxane resin may be selectively modified by changing R. For example, when a majority of R in the organopolysiloxane resin are univalent aliphatic hydrocarbon groups, such as methyl groups, the refractive index of the organopolysiloxane resin may be less than 1.5. Alternatively, if a majority of R in the organopolysiloxane resin are univalent aromatic hydrocarbon groups, such as phenyl groups, the refractive index may be greater than 1.5. This value can be readily controlled by substitution of the organopolysiloxane resin, or by inclusion of additional components in the curable composition, as described below.

In certain embodiments, at least 15 mole %, alternatively at least 20 mole %, alternatively at least 25 mole %, of all organic groups of the organopolysiloxane resin comprise univalent aromatic hydrocarbon groups, e.g. phenyl groups. If the organopolysiloxane resin comprises fewer univalent aromatic carbon groups, the cured product obtained from the curable composition will have a reduced light transmittance in the range of communication wavelengths.

In various embodiments of the organopolysiloxane resin, siloxane units having a cationic polymerizable group constitute from 2 to 70, alternatively from 10 to 40, alternatively 15 to 40, mole % of all siloxane units. If such siloxane units are present in the organopolysiloxane resin in an amount below 2 mole %, this will lead to a decrease in a degree of cross-linking during curing of the curable composition, which decreases hardness of the cured product formed therefrom. If, on the other hand, the content of these siloxane units exceeds 70 mole % in the organopolysiloxane resin, the cured product may have reduced visible light transmittance, low resistance to heat, and increased brittleness.

Typically, the cationic polymerizable groups are not directly bonded to silicon atoms of the organopolysiloxane resin. Instead, the cationic polymerizable groups are generally bonded to silicon atoms via a bivalent linking group, such as a hydrocarbylene, heterohydrocarbylene, or organoheterylene linking group.

For example, when the cationic polymerizable groups are cyclic ether groups, e.g. epoxy groups, specific examples of cationic polymerizable groups suitable for the organopolysiloxane resin are set forth immediately below:

3-(glycidoxy) propyl group:

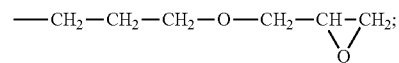

2-(glycidoxycarbonyl) propyl group:

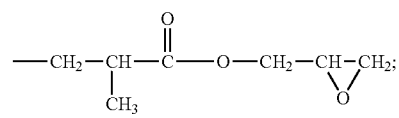

2-(3,4-epoxycyclohexyl) ethyl group:

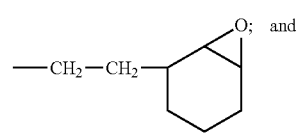

2-(4-methyl-3,4-epoxycyclohexyl) propyl group:

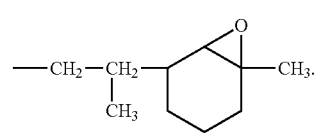

Additional examples of cyclic ether groups suitable for the cationic polymerizable group include the following: 2-glycidoxyethyl, 4-glycidoxybutyl, or similar glycidoxyalkyl groups; 3-(3,4-epoxycyclohexyl)propyl, or similar 3,4-epoxycyclohexylalkyl groups; 4-oxiranylbutyl, 8-oxiranyloctyl, or similar oxiranylalkyl groups. In these embodiments, the cationic polymerizable material may be referred to as an epoxy-functional silicone material.

Specific examples of cationic polymerizable groups other than the epoxy groups exemplified above include, but are not limited to, the following groups (with the left-most portion representing the bond connecting the particular cationic polymerizable group to the organopolysiloxane resin):

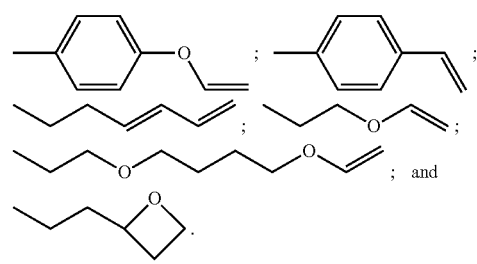

Specific examples of the organopolysiloxane resin when the cationic polymerizable groups are cyclic ether groups, e.g. epoxy groups, include organopolysiloxane resins comprising or consisting of the following sets of: ($Me_2SiO_{2/2}$), ($PhSiO_{3/2}$), and ($E^1SiO_{3/2}$) units; ($Me_3SiO_{1/2}$), ($Me_2SiO_{3/2}$), (PhSiO$_{3/2}$), and (E$^1$SiO$_{3/2}$) units; (Me$_2$SiO$_{2/2}$), (PhSiO$_{3/2}$), (E$^1$SiO$_{3/2}$) and (SiO$_{4_{1_2}}$) units; (Me$_2$SiO$_{2/2}$), (PhSiO$_{3/2}$), (MeSiO$_{3/2}$), and (E$^1$SiO$_{3/2}$) units; (Ph$_2$SiO$_{2/2}$), (PhSiO$_{3/2}$), and (E$^1$SiO$_{3/2}$) units; (MePhSiO$_{2/2}$), (PhSiO$_{3/2}$), and (E$^1$SiO$_{3/2}$) units; (Me$_2$SiO$_{2/2}$), (PhSiO$_{3/2}$), and (E$^2$SiO$_{3/2}$) units; (Me$_2$SiO$_{2/2}$), (PhSiO$_{3/2}$), and (E$^3$SiO$_{3/2}$) units; (Me$_2$SiO$_{2/2}$), (PhSiO$_{3/2}$), and (E$^4$SiO$_{3/2}$) units; (MeViSiO$_{2/2}$), PhSiO$_{3/2}$), and (E$^3$SiO$_{3/2}$) units; (Me$_2$SiO$_{2/2}$), (PhSiO$_{3/2}$), (MeSiO$_{3/2}$), and (E$^3$SiO$_{3/2}$) units; (Ph$_2$SiO$_{2/2}$), (PhSiO$_{3/2}$), and (E$^3$SiO$_{3/2}$) units; (Me$_2$SiO$_{2/2}$), (Ph$_2$SiO$_{2/2}$), and (E$^1$SiO$_{3/2}$) units; (Me$_2$SiO$_{2/2}$), (Ph$_2$SiO$_{2/2}$), and (E$^3$SiO$_{3/2}$) units; (Me$_2$ViSiO$_{1/2}$), (Me$_2$SiO$_{2/2}$), (PhSiO$_{3/2}$), and (E$^1$SiO$_{3/2}$) units; (Me$_3$SiO$_{1/2}$), (Ph$_2$SiO$_{2/2}$), (PhSiO$_{3/2}$), and (E$^1$SiO$_{3/2}$) units; (Me$_3$SiO$_{1_2}$), (Me$_2$SiO$_{2/2}$), (PhSiO$_{3/2}$), and (E$^3$SiO$_{3/2}$) units; (Me$_2$SiO$_{2/2}$), (PhSiO$_{3/2}$), (E$^3$SiO$_{3/2}$), and (SiO$_2$) units; (Me$_2$SiO$_{2/2}$), (Ph$_2$SiO$_{2/2}$), (E$^1$SiO$_{3/2}$), and (SiO$_2$) units; (Me$_3$SiO$_{1_2}$), (Me$_2$SiO$_{2/2}$), (PhSiO$_{3/2}$), (E$^1$SiO$_{3/2}$), and (SiO$_2$) units; and (Me$_3$SiO$_{1/2}$), (Me$_2$SiO$_{2/2}$), (PhSiO$_{3/2}$), (E$^3$SiO$_{3/2}$), and (SiO$_2$) units; where Me designates a methyl group, Vi designates a vinyl group, Ph designates a phenyl group, E$^1$ designates a 3-(glycidoxy)propyl group, E$^2$ designates a 2-(glycidoxycarbonyl)propyl group, E$^3$ designates a 2-(3,4-epoxycyclohexyl)ethyl group, and E$^4$ designates 2-(4-methyl-3,4-epoxycyclohexyl)propyl group. The same designations are applicable to the following description herein. It is contemplated that any of the univalent hydrocarbon substituents exemplified in the organopolysiloxane resins above (e.g. Me, Ph, and Vi) may be replaced by other univalent hydrocarbon substituents. For example, an ethyl group or other substituted or unsubstituted hydrocarbyl group may be utilized in place of any of the methyl, phenyl, or vinyl groups above. Further, cationic polymerizable groups other than E$^1$-E$^4$ may be utilized in place of or in addition to E$^1$-E$^4$. However, the species of organopolysiloxane resin identified above are particularly desirable due to their refractive index values and physical properties.

Such organopolysiloxane resins may be prepared by conventional methods. For example, these organopolysiloxane resins may be prepared by any of the following methods: a method in which a silane of formula R$^4$R$^5$SiCl$_2$ and a silane of formula R$^6$SiCl$_3$ are cohydrolyzed and condensed; a method in which a silane of formula R$^4$R$^5$SiCl$_2$, a silane of formula R$^6$SiCl$_3$ and a silane of formula R$^1$R$^2$R$^3$SiCl are cohydrolyzed and condensed; a method in which a silane of formula R$^4$R$^5$SiCl$_2$, a silane of formula R$^6$SiCl$_3$ and a silane of formula SiCl$_4$ are cohydrolyzed and condensed; a method in which a silane of formula R$^4$R$^5$SiCl$_2$, a silane of formula R$^6$SiCl$_3$, a silane of formula R$^1$R$^2$R$^3$SiCl, and a silane of formula SiCl$_4$ are cohydrolyzed and condensed; and a method in which silanes bearing silicon-bonded hydrolysable groups other than silicon-bonded halogen atoms are cohydrolyzed and condensed.

The organopolysiloxane resin may have some residual silicon-bonded alkoxy groups and/or silicon-bonded hydroxyl groups (i.e., silanol groups) from its preparation. The content of these groups may depend on the method of manufacture and manufacturing conditions. These substituents may affect storage stability of the organopolysiloxane resin and reduce thermal stability of the cured product formed from the organopolysiloxane resin. Therefore, in certain embodiments, it is desirable to restrict the formation of such groups. For example, the amount of silicon-bonded alkoxy groups and silicon-bonded hydroxyl groups can be reduced by heating the organopolysiloxane resin in the presence of a minute quantity of potassium hydroxide, thus causing a dehydration and condensation reaction or a de-alcoholation and condensation reaction. It is recommended that the content of these substituents be no more than 2 mole % and preferably no more than 1 mole % of all substituents on silicon atoms.

Although there are no special restrictions with regard to the number-average molecular weight (M$_n$) of the organopolysiloxane resin, the organopolysiloxane resin has, in certain embodiments, a M$_n$ between 10$^3$ and 10$^6$ Daltons.

The curable composition further comprises a diluent component. The diluent component comprises a silane compound having a single (i.e., only one) silicon-bonded cationic polymerizable group.

The single silicon-bonded cationic polymerizable group may be any of the cationic polymerizable groups described above.

The silane compound generally has a dynamic viscosity of less than 1,000, alternatively less than 500, alternatively less than 100, alternatively less than 50, alternatively less than 25, alternatively less than 10, cP at 25° C. In these embodiments, the silane compound has a boiling point temperature of at least 25, alternatively at least 50, alternatively at least 75, alternatively at least 80, alternatively at least 85, alternatively at least 90, ° C. at a pressure of 1 mm Hg (133.32 Pascals). For example, in certain embodiments, the silane compound has a boiling point temperature of from 80 to 120, alternatively from 90 to 110, ° C. at a pressure of 1 mm Hg.

In certain embodiments, the silane compound of the diluent component is free from any silicon-bonded hydrolysable groups other than potentially the cationic polymerizable group. For example, certain silicon-bonded hydrolysable groups, such as silicon-bonded halogen atoms, react with water to form silanol (SiOH) groups, wherein the silicon-halogen bond has been cleaved. Other silicon-bonded hydrolysable groups, such as a carboxylic ester, may hydrolyze without cleaving any bond to silicon. To this end, in certain embodiments, the silane compound is free from any silicon-bonded hydrolysable groups that may hydrolyze to form silanol groups. In other embodiments, the cationic polymerizable group of the silane compound is not hydrolysable such that the silane compound is free from any silicon-bonded hydrolysable groups altogether. In these embodiments, the cationic polymerizable group is not hydrolysable, e.g. the cationic polymerizable group is a cyclic ether. Specific examples of hydrolysable groups include the following silicon-bonded groups: a halide group, an alkoxy group, an alkylamino group, a carboxy group, an alkyliminoxy group, an alkenyloxy group, and an N-alkylamido group. For example, certain conventional silane compounds may have, in addition to more than one cationic polymerizable group, a silicon-bonded alkoxy group. Such silicon-bonded alkoxy groups may hydrolyse and condense, forming siloxane bonds and increasing a cross-link density of the cured product. In contrast, the silane compound is generally utilized to reduce a cross-link density of the cured product, and thus these hydrolysable groups are, in certain embodiments, undesirable.

In various embodiments, the silane compound of the diluent component has the following general formula:

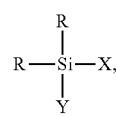

where R is independently selected and defined above, Y is the cationic polymerizable group, and X is selected from R and SiR$_3$.

In certain embodiments, X is R such that the silane compound comprises a monosilane compound. In these embodiments, the silane compound has the general formula YSiR$_3$, where Y and R are defined above. When Y is independently selected from E$^1$-E$^4$ above, the silane compound may be rewritten as, for example, E$^1$SiR$_3$, E$^2$SiR$_3$, E$^3$SiR$_3$, and E$^4$SiR$_3$. Of E$^1$-E$^4$, E$^3$ is most typical.

In other embodiments, X is SiR$_3$ such that the silane compound comprises a disilane compound. In these embodiments, the single cationic polymerizable group may be bonded to either silicon atom of the disilane, which silicon atoms are typically directly bonded to one another (in the absence of an O heteroatom, in which case the silane compound would be a disiloxane). Although R is independently selected from substituted and unsubstituted hydrocarbyl groups, R is most typically selected from alkyl groups and aryl groups for controlling the refractive index of the cured product of the curable composition.

Specific examples of the silane compound in embodiments in which the cationic polymerizable group of the silane compound is E$^3$ are set forth immediately below:

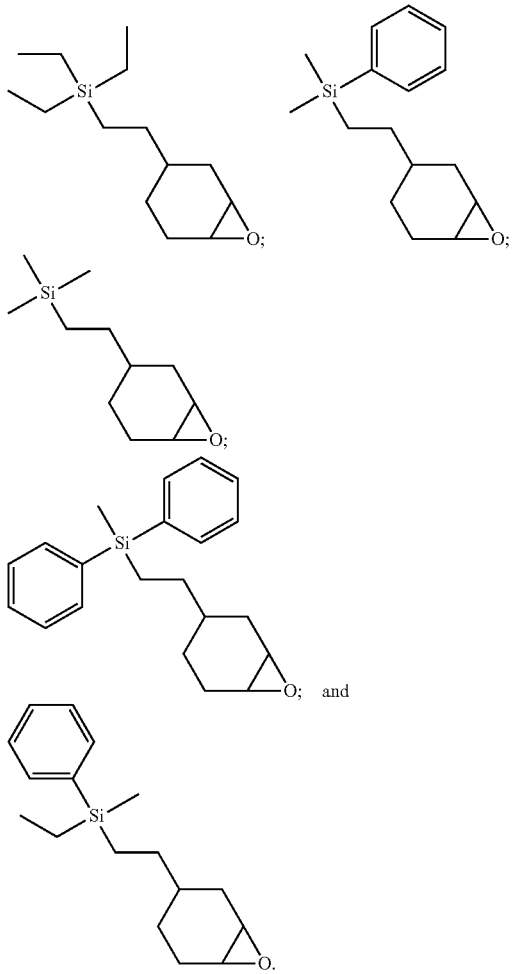

Additional examples of the silane compound include, but are not limited to, the following:

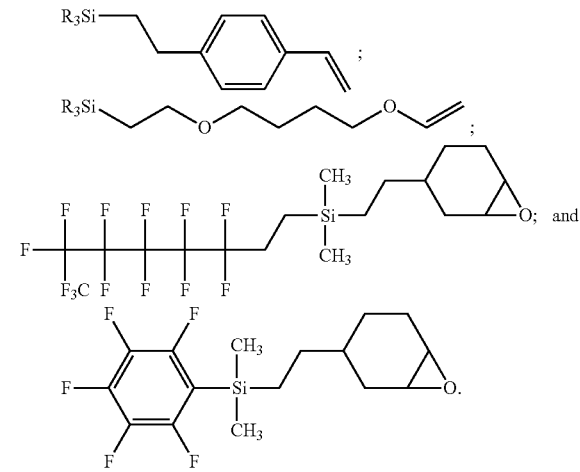

Such silane compounds may be prepared via various methods. For example, the starting reactants are generally chosen based on the desired substitution (R and Y) in the silane compound. To this end, in one embodiment, the silane compound is prepared via hydrosilylation. For example, the first silane compound exemplified above may be prepared in accordance with the following reaction mechanism:

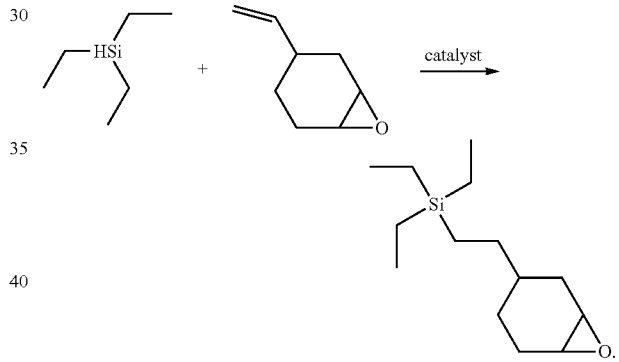

The catalyst may be any hydrosilylation catalyst, which is typically a platinum group metal. One of skill in the art recognizes how to modify the starting reactants based on the desired silane compound to prepare and obtain silane compounds having structures other than the structure exemplified above.

The silane compound of the diluent component advantageously has a single silicon-bonded cationic polymerizable group. Conventional diluents generally include at least two epoxy groups and potentially additional hydrolysable groups. Conventional diluents including at least two epoxy groups contribute to an increased cross-link density of the cured product formed from the curable composition, which is undesirable in certain applications in which the cured product may be utilized, e.g. various optical articles. Further, the instant silane compound may effectively solubilize the cationic polymerizable material, e.g. the organopolysiloxane resin, thus obviating the need for another solvent in the curable composition. In addition, conventional diluents are generally carbon-based. Some carbon-based diluents include a single cationic polymerizable group, but such carbon-based diluents are generally highly volatile and/or toxic. To reduce volatility thereof, many carbon-based diluents include long-chain substitution. However, such substitution undesirably increases viscosity. In contrast, the instant silane compound of the instant invention has a reduced volatility (and vapor pressure) while simultaneously possessing a desirably low viscosity. The silane compound also can be utilized to adjust or selectively control the refractive index of the curable composition, along with the substitution of the cationic polymerizable material (e.g. the organopolysiloxane resin) and thus the relative amount of the silane compound utilized may be modified to selectively control the refractive index of the curable composition.

The diluent component typically comprises the silane compound in an amount sufficient to provide at least 3, alternatively at least 5, alternatively at least 10, alternatively at least 15, alternatively at least 20, alternatively at least 25, alternatively at least 30, percent by weight of the silane compound based on the total weight of the curable composition. The relative amount of the silane compound present in the curable composition may vary based on the presence or absence of certain optional components, such as solvent, as described below. To this end, the values set forth above are typical when the curable composition is solventless (but for the diluent component, which may act as a solvent in the curable composition).

The diluent component may not, alternatively may, comprise compounds or components in addition to the silane compound. For example, the diluent component may comprise a diluent compound other than and in addition to the silane compound. The diluent compound may differ from the silane compound in various respects. For example, the diluent compound may have more than one cationic polymerizable group. Alternatively, the diluent compound may have a single cationic polymerizable group, but may be free from silicon. The diluent component may comprise more than one diluent compound, i.e., the diluent component may comprise any combination of diluent compounds. The diluent compound may be aromatic, alicyclic, aliphatic, etc.

Specific examples of aromatic diluent compounds suitable for the diluent component include polyglycidyl ethers of polyhydric phenols each having at least one aromatic ring, or of alkylene oxide adducts of the phenols such as glycidyl ethers of bisphenol A and bisphenol F, or of compounds obtained by further adding alkylene oxides to bisphenol A and bisphenol F; and epoxy novolak resins.

Specific examples of alicyclic diluent compounds suitable for the diluent component include polyglycidyl ethers of polyhydric alcohols each having at least one alicyclic ring; and cyclohexene oxide- or cyclopentene oxide-containing compounds obtained by epoxidizing cyclohexene ring- or cyclopentene ring-containing compounds with oxidants. Examples include a hydrogenated bisphenol A glycidyl ether, 2-(3,4-epoxycyclohexyl-5,5-spiro-3,4-epoxy)cyclohexane-methadioxane, bis(3,4-epoxycyclohexylmethyl)adipate, vinylcyclohexene dioxide, 4-vinylepoxycyclohexane, bis(3,4-epoxy-6-methylcyclohexylmethyl)adipate, 3,4-epoxy-6-methylcyclohexylcarboxylate, dicyclopentadienediepoxide, ethyleneglycol di(3,4-epoxycyclohexylmethyl)ether, dioctyl epoxyhexahydrophthalate and di-2-ethylhexyl epoxyhexahydrophthalate.

Specific examples of aliphatic diluent compounds suitable for the diluent component include polyglycidyl ethers of aliphatic polyhydric alcohols and the alkyleneoxide adducts of the aliphatic polyhydric alcohols; polyglycidyl esters of aliphatic long-chain polybasic acid, homopolymers synthesized by the vinyl polymerization of glycidyl acrylate or glycidyl methacrylate, and copolymers synthesized by the vinyl polymerization of glycidyl acrylate and another vinyl polymer. Representative compounds include glycidyl ethers of polyhydric alcohols, such as 1,4-butanediol diglycidyl ether, 1,6-hexanediol diglycidyl ether, triglycidyl ethers of glycerine, triglycidyl ethers of trimethylolpropane, tetraglycidyl ethers of sorbitol, hexaglycidyl ethers of dipentaerythritol, diglycidyl ethers of polyethylene glycol, diglycidyl ethers of polypropyleneglycol, polyglycidyl ethers of polyether polyol obtained by adding one, two or more kinds of alkyleneoxides with an aliphaticpolyhydric alcohol such as propyleneglycol, trimethylol propane or glycerine, and diglycidyl esters of aliphatic long-chain dibasic acids. In addition, monoglycidyl ethers of aliphatic higher alcohols, phenol, cresol, butylphenol, monoglycidyl ethers of polyether alcohols obtained by adding alkyleneoxide to them, glycidyl esters of higher aliphatic acids, epoxidized soy-bean oil, octyl epoxystarate, butyl epoxystearate, epoxidized linseed oil, epoxidized polybutadiene, and the like are exemplified.

Additional examples of diluent compounds suitable for the diluent component include oxetane compounds, such as trimethylene oxide, 3,3-dimethyl oxetane and 3,3-dichloromethyl oxetane; trioxanes, such as tetrahydrofuran and 2,3-dimethyltetrahydrofuran; cyclic ether compounds, such as 1,3-dioxolane and 1,3,6-trioxacyclooctane; cyclic lactone compounds, such as propiolactone, butyrolactone and caprolactone; thiirane compounds, such as ethylene sulfide; thiethane compounds, such as trimethylene sulfide and 3,3-dimethylthiethane; cyclic thioether compounds, such as tetrahydrothiophene derivatives; spiro ortho ester compounds obtained by a reaction of an epoxy compound and lactone; and vinyl ether compounds such as ethyleneglycol divinyl ether, alkylvinyl ether, 3,4-dihydropyran-2-methyl (3,4-dihydropyran-2-methyl(3,4-dihydrpyra-ne-2-carboxylate) and triethyleneglycol divinyl ether.

If present, the diluent component typically comprises the diluent compound in an amount sufficient to provide from greater than 0 to 30, alternatively from greater than 0 to 10, alternatively from 1 to 5, percent by weight of the diluent compound based on the total weight of the curable composition. These values generally reflect any cationic polymerizable diluent compound other than the silane compound in the diluent component, i.e., when a combination of different diluent compounds are utilized, the values above represent their collective amounts. In certain embodiments, the diluent component comprises the silane compound and the diluent compound.

The curable composition generally further comprises a catalyst. The catalyst is effective for enhancing curing of the curable composition. When the cationic-polymerizable material is curable upon exposure to active-energy rays, the catalyst may be referred to as a photocatalyst. However, catalysts other than photocatalysts may be utilized, e.g. when the curable composition is cured upon exposure to heat as opposed to active-energy rays. The photocatalyst may alternatively be referred to as a photopolymerization initiator, and generally serves to initiation photopolymerization of the cationic polymerizable material and the diluent component. The catalyst may comprise any catalyst suitable for such polymerization. Examples of catalysts may include sulfonium salts, iodinium salts, selenonium salts, phosphonium salts, diazonium salts, paratoluene sulfonate, trichloromethyl-substituted triazine, and trichloromethyl-substituted benzene. Additional catalysts include acid generators, which are known in the art. The catalyst may increase rate of curing the curable composition, decrease time to onset of curing, increase extent of crosslinking of the curable composition, increase crosslink density of the cured product, or a combination of any two or more thereof. Typically, the catalyst at least increases the rate of curing the curable composition.

The sulfonium salts suitable for the catalyst may be expressed by the following formula: $R^7_3S^+X^-$, where $R^7$ may designated a methyl group, ethyl group, propyl group, butyl group, or a similar alkyl group with 1 to 6 carbon atoms; a phenyl group, naphthyl group, biphenyl group, tolyl group, propylphenyl group, decylphenyl group, dodecylphenyl group, or a similar aryl or a substituted-aryl group with 6 to 24 carbon atoms. In the above formula, $X^-$ represents $SbF_6^-$, $AsF_6^-$, $PF_6^-$, $BF_4^-$, $B(C_6F_5)_4^-$, $HSO_4^-$, $ClO_4^-$, $CF_3SO_3^-$, or similar non- nucleophilic, non-basic anions. The iodonium salts can be represented by the following formula: $R^7_2I^+X^-$, where $R^7$ is the same as $X^-$ defined above. The selenonium salt can be represented by the following formula: $R^7_3Se^+X^-$, where $R^7$, $X^-$ are the same as defined above. The phosphonium salt can be represented by the following formula: $R^7_4P^+X^-$, wherein $R^7$, $X^-$ are the same as defined above. The diazonium salt can be represented by the following formula: $R^7N_2^+X^-$, where $R^7$ and $X^-$ are the same as defined above. The para-toluene sulfonate can be represented by the following formula: $CH_3C_6H_4SO_3R^8$, wherein $R^8$ is an organic group that contains an electron-withdrawing group, such as a benzoylphenylmethyl group, or a phthalimide group. The trichloromethyl-substituted triazine can be represented by the following formula: $[CCl_3]_2C_3N_3R^9$, wherein $R^9$ is a phenyl group, substituted or unsubstituted phenylethynyl group, substituted or unsubstituted furanylethynyl group, or a similar electron-withdrawing group. The trichloromethyl-substituted benzene can be represented by the following formula: $CCl_3C_6H_3R^7R^{10}$, wherein $R^7$ is the same as defined above, $R^{10}$ is a halogen group, halogen-substituted alkyl group, or a similar halogen-containing group.

Specific examples of catalysts suitable for the curable composition include triphenylsulfonium tetrafluoroborate, triphenylsulfonium hexafluoroantimonate, triphenylsulfonium trifurate, tri(p-tolyl)sulfonium hexafluorophosphate, p-tertiarybutylphenyl diphenylsulfonium hexafluoroantimonate, diphenyliodonium tetrafluoroborate, diphenyliodonium hexafluoroantimonate, p-tertiarybutylphenyl biphenyliodonium hexafluoroantimonate, di(p-tertiarybutylphenyl) iodonium hexafluoroantimonate, bis(dodecylphenyl) iodonium hexafluoroantimonate, triphenylselenonium tetrafluoroborate, tetraphenylphosphonium tetrafluoroborate, tetraphenylphosphonium hexafluoroantimonate, p-chlorophenyldiazonium tetrafluoroborate, benzoylphenyl paratolyenesulfonate, bistrichloromethylphenyl triazine, bistrichloromethyl furanyltriazine, p-bistrichloromethyl benzene, etc.

The catalyst may comprise two or more different species, optionally in the presence of a carrier solvent.

The catalyst may be present in the curable composition in varying amounts. Generally, the catalyst is present in an amount sufficient to initiate polymerization and curing of the curable composition upon exposure to active-energy rays (i.e., high-energy rays), such as ultraviolet rays. In certain embodiments, the catalyst is utilized in an amount of from greater than 0 to 5, alternatively from 0.1 to 4, percent by weight based on the total weight of the curable composition.

As introduced above, the curable composition may be free from another solvent other than the diluent component, in the event the diluent component is considered a solvent. In these embodiments, the diluent component generally solubilizes the cationic polymerizable material sufficient to pour and wet coat the curable composition. However, if desired, the curable composition may further comprise a solvent, e.g. an organic solvent.

The solvent may be utilized when the curable composition is otherwise in a solid state or is a highly-viscous liquid, i.e., when the diluent compound is utilized in a minimal amount. The solvent, if utilized, is generally selected for miscibility with the cationic polymerizable material and the diluent component. Generally, the solvent has a boiling point temperature of from 80° C. to 200° C. at atmospheric pressure, which allows for the solvent to be removed via heat or other methods when curing the curable composition. Specific examples of solvents suitable for the curable composition include isopropyl alcohol, tertiarybutyl alcohol, methylethylketone, methylisobutylketone, toluene, xylene, mesitylene, chlorobenzene, ethyleneglycoldimethylether, ethyleneglycoldiethylether, diethyleneglycoldimethylether, ethoxy-2-propanolacetate, methoxy-2-propanolacetate, octamethylcyclotetrasiloxane, hexamethyldisiloxane, etc. The curable composition may comprise a combination of different solvents. The solvent, if utilized, may be present in an amount sufficient to solubilize the cationic polymerizable material and the diluent component such that the curable composition has a viscosity which lends itself to pouring. The solvent referred to herein is not with regards to any carrier solvent for the catalyst. For example, the curable composition may be referred to as solventless while still utilizing a carrier solvent along with the catalyst. Solventless, as used herein with reference to the curable composition being solventless, means that total solvent, including any carrier solvent, may be present in the curable composition in an amount of less than 5, alternatively less than 4, alternatively less than 3, alternatively less than 2, alternatively less than 1, alternatively less than 0.1, percent by weight based on the total weight of the curable composition.

The curable composition may optionally and additionally include any other suitable component(s), such as a coupling agent, an antistatic agent, an ultraviolet absorber, a plasticizer, a leveling agent, a pigment, a catalyst, an inhibitor of the catalyst, and so on. The inhibitor of the catalyst may function to prevent or slow rate of curing until the catalyst is activated (e.g. by removing or deactivating the inhibitor).

In certain embodiments, the curable composition is in the form of a liquid with a dynamic viscosity of from 20 to 10,000 mPa·s at 25° C.

As introduced above, the present invention also provides a method of preparing a cured article. The method comprises applying the curable composition on a substrate to form a film, and curing the film on the substrate to form the cured article.

The curable composition may be applied on the substrate via various methods. For example, in certain embodiments, the step of applying the curable composition on the substrate comprises a wet coating method. Specific examples of wet coating methods suitable for the method include dip coating, spin coating, flow coating, spray coating, roll coating, gravure coating, sputtering, slot coating, and combinations thereof.

The substrate may be rigid or flexible. Examples of suitable rigid substrates include inorganic materials, such as glass plates; glass plates comprising an inorganic layer; ceramics; wafers, such as silicon wafers, and the like. In other embodiments, it may be desirable for the cured article to be flexible, in which case the substrate itself is typically flexible. In these embodiments, specific examples of flexible substrates include those comprising various organic polymers. From the view point of transparency, refractive index, heat resistance and durability, specific examples of flexible substrates include those comprising polyolefins (polyethylene, polypropylene, etc.), polyesters (poly(ethylene terephthalate), poly(ethylene naphthalate), etc.), polyamides (nylon 6, nylon 6,6, etc.), polystyrene, poly(vinyl chloride), polyimides, polycarbonates, polynorbornenes, polyurethanes, poly(vinyl alcohol), poly(ethylene vinyl alcohol), polyacrylics, celluloses (triacetylcellulose, diacetylcellulose, cellophane, etc.), or interpolymers (e.g., copolymers) of such organic polymers. As understood in the art, the organic polymers recited above may be rigid or flexible. Further, the substrate may be reinforced, e.g. with fillers and/or fibers.

The curable composition, as well as the film formed therefrom, can be rapidly cured by being irradiated with active-energy rays (i.e., high-energy rays). The active-energy rays may comprise ultraviolet rays, electron beams, or other electromagnetic waves or radiation. The use of ultraviolet rays is preferable from the point of view of low cost and high stability. A source of ultraviolet radiation may comprise a high-pressure mercury lamp, medium-pressure mercury lamp, Xe—Hg lamp, or a deep UV lamp.

The step of curing the film generally comprises exposing the film to radiation at a dosage sufficient to cure at least a portion, alternatively the entirety, of the film. The dosage of radiation for curing the film is typically from 100 to 8000 mJ/cm$^2$. In certain embodiments, heating is used in conjunction with irradiation for curing the film. For example, the film may be heated before, during, and/or after irradiating the film with active-energy rays. While active energy-rays generally initiate curing of the curable composition, residual solvents may be present in the cationic polymerizable material, which may be volatilized and driven off by heating. Typical heating temperatures are in the range of from 50 to 200° C. Curing the film results in the preparation of the cured article, and the film, once cured, is referred to herein as the cured product.

The cured product typically possesses hardness and elasticity without deformation, buckling, or formation of cracks. These properties allow the use of the curable composition in the form of films and thin-film elements. Further, the cured product is characterized by high light transmittance with minimal light-transmission losses. The refractive index can be selectively controlled. Similarly, the cured product has excellent shape stability and resistance to solvents, is characterized by high coefficient of light transmittance in the range of communication wavelengths, and has minimal variations in light transmittance and refractive index. The cured product generally has a light transmittance of at least 90, alternatively at least 95, alternatively at least 96, alternatively at least 97, alternatively at least 98, alternatively at least 99, percent in the range of visible light. These physical properties are particularly desirable in certain optical applications.

The refractive index of the cured product may be selectively modified by changing a mole ratio of univalent aliphatic hydrocarbon groups (typically, methyl groups) and univalent aromatic hydrocarbon groups (typically, phenyl groups) that comprise substituents of the cationic polymerizable material. An increase in the proportion of the univalent aromatic hydrocarbon groups increases the refractive index, while an increase in the share of the univalent aliphatic groups decreases the refractive index.

The curable composition is particularly suitable for the fabrication or manufacture of waveguides. For example, the curable composition may be utilized in the fabrication method disclosed in Application Ser. No. 61/824,425, which is filed herewith and is incorporated by reference in its entirety. Alternatively, the curable composition may be utilized in conventional fabrication methods. In these conventional fabrication methods, a curable composition for the cladding layer is applied by spin coating onto a substrate, and the applied material is cured by irradiation with active-energy rays to form a lower cladding layer. Following this, a second curable composition for the core layer is applied by spin coating onto the lower cladding layer and, if necessary, the core layer is subjected to forming for imparting to it a desired shape, and is then cured to form a cured core layer with the refractive index greater than that of the cladding layer. The core layer may be treated for imparting to it a desired shape, e.g., for patterning. This shape can be formed by exposing the core layer to active-energy rays through a drawn mask, if necessary, with subsequent heating, and the unexposed areas are removed by dissolving with an organic solvent. The surface of the core layer, or of the patterned core layer, and of the lower cladding layer is coated with the curable composition intended specially for cladding (which may be the same as or different from the curable composition utilized to form the lower lading layer), and after the curable composition is cured and the formation of the upper cladding layer is completed, a film-type optical waveguide having a cladding-core-cladding structure is produced.

When the curable composition is utilized in the manufacture of optical waveguides, it is generally required that the cured product intended for the core portion has a higher refractive index than the cured product of the intended for the cladding portion. Therefore, curable composition intended for the core portion should have a greater content of the univalent aromatic hydrocarbon groups than the curable composition intended for the cladding portion. In view of the above, it is possible to utilize separation methods for separating two different types of curable compositions for core and cladding portions.

The cured product and cured article are applicable for both passive-system elements and active-system elements. The following are examples of such applications: non-branched type optical waveguides, wave division multiplexers [WDM], branched optical waveguide, optical adhesives or similar passive light-transmitting elements, optical waveguide switches, optical attenuators, and optical amplifiers or similar active light-transmitting elements.

If desired, the cured product may be separated from the substrate, in which case the cured product is a free-standing film. Similarly, the waveguide itself may be removed or separated from the substrate.

The curable composition and method of the present invention have significantly improved properties as compared to conventional compositions. For example, as more flexible cured products are desired, it has been found that heating at elevated temperatures generally causes separation and curling of the cured product from the substrate. This is generally due to differences in coefficients of thermal expansion between the cured product and the substrate, which may undesirably cause curling of the substrate or the cured product after curing. Attempts to minimize such curling have been pursued, e.g. by use of plasticizers like bis 2-ethylhexyl adipate, but such attempts make it difficult, if not impossible, to apply additional layers on the cured product due to localized areas of different surface tension in the cured product due to separation of the plasticizers therein. Other diluents are highly volatile and have undesirable environmental and health profiles.

Some additional aspects of the present invention are as follows:

Aspect 1: A curable composition comprising a cationic polymerizable material and a diluent component comprising a silane compound having a single silicon-bonded cationic polymerizable group.

Aspect 2: The curable composition of Aspect 1 wherein said cationic polymerizable material comprises an epoxy-functional silicone material.

Aspect 3: The curable composition of Aspect 2 wherein said cationic polymerizable group is selected from a cyclic ether group, a cyclic ester group, a thietane group, a dioxepane group, a cyclic carbonate group, a vinyl ether group, a divinyl ether group, a vinyl ester group, a diene group, a tertiary vinyl group, a styrene group, and a styrene derivative group.

Aspect 4: The curable composition of any one of Aspects 1-3 wherein said silane compound is free from any silicon-bonded hydrolysable groups.

Aspect 5: The curable composition of Aspect 1 wherein said silane compound has the following general formula:

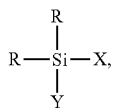

where R is an independently selected substituted or unsubstituted hydrocarbyl group, Y is said single silicon-bonded cationic polymerizable group, and X is selected from R and $SiR_3$.

Aspect 6: The curable composition of any one of Aspects 1-5 wherein said silane compound has a viscosity of less than 1,000 cP at 25° C.

Aspect 7: The curable composition of any one of Aspects 1-6 wherein said diluent compound further comprises a cationic polymerizable compound other than said silane compound.

Aspect 8: The curable composition of any one of Aspects 1-7 wherein said epoxy-functional silicone material comprises an epoxy-functional silicone resin.

Aspect 9: The curable composition of any one of Aspects 1-8 further comprising a catalyst.

Aspect 10: The curable composition of any one of Aspects 1-9 wherein said silane compound of said diluent component is present in said curable silicone composition in an amount of at least 3% by weight based on the total weight of said curable silicone composition.

Aspect 11: A method of preparing a cured article, said method comprising applying the curable composition of Aspect 1 on a substrate to form a film; and curing the film on the substrate to form the cured article.

Aspect 12: The method of Aspect 11 wherein the substrate comprises a flexible polymeric substrate.

Aspect 13: The method of Aspect 11 or Aspect 12 wherein curing the film comprises exposing the film to radiation at a dosage sufficient to cure the film.

Aspect 14: The method of Aspect 11 or Aspect 12 wherein curing the film comprises exposing at least one portion of the film to radiation at a dosage sufficient to cure the at least one portion of the film.

Aspect 15: A cured article formed in accordance with the method of Aspect 11.

Aspect 16: A waveguide comprising a cured article formed in accordance with the method of Aspect 11.

It is to be understood that the appended claims are not limited to express and particular compounds, compositions, or methods described in the detailed description, which may vary between particular embodiments which fall within the scope of the appended claims. With respect to any Markush groups relied upon herein for describing particular features or aspects of various embodiments, different, special, and/or unexpected results may be obtained from each member of the respective Markush group independent from all other Markush members. Each member of a Markush group may be relied upon individually and or in combination and provides adequate support for specific embodiments within the scope of the appended claims.

Further, any ranges and subranges relied upon in describing various embodiments of the present invention independently and collectively fall within the scope of the appended claims, and are understood to describe and contemplate all ranges including whole and/or fractional values therein, even if such values are not expressly written herein. One of skill in the art readily recognizes that the enumerated ranges and subranges sufficiently describe and enable various embodiments of the present invention, and such ranges and subranges may be further delineated into relevant halves, thirds, quarters, fifths, and so on. As just one example, a range "of from 0.1 to 0.9" may be further delineated into a lower third, i.e., from 0.1 to 0.3, a middle third, i.e., from 0.4 to 0.6, and an upper third, i.e., from 0.7 to 0.9, which individually and collectively are within the scope of the appended claims, and may be relied upon individually and/or collectively and provide adequate support for specific embodiments within the scope of the appended claims. In addition, with respect to the language which defines or modifies a range, such as "at least," "greater than," "less than," "no more than," and the like, it is to be understood that such language includes subranges and/or an upper or lower limit. As another example, a range of "at least 10" inherently includes a subrange of from at least 10 to 35, a subrange of from at least 10 to 25, a subrange of from 25 to 35, and so on, and each subrange may be relied upon individually and/or collectively and provides adequate support for specific embodiments within the scope of the appended claims. Finally, an individual number within a disclosed range may be relied upon and provides adequate support for specific embodiments within the scope of the appended claims. For example, a range "of from 1 to 9" includes various individual integers, such as 3, as well as individual numbers including a decimal point (or fraction), such as 4.1, which may be relied upon and provide adequate support for specific embodiments within the scope of the appended claims.

The following examples are intended to illustrate the invention and are not to be viewed in any way as limiting to the scope of the invention.

EXAMPLES

Preparation Example 1

A cationic polymerizable material was prepared. In particular, a 5 L three-neck round bottom flask equipped with a thermometer, mechanical stirrer, and condenser was loaded with 910.5 g of silicone resin (77% NVC in toluene), 305 g of trimethoxy[2-(7-oxabicyclo[4.1.0]hept-3-yl)ethyl]silane, 351 g of dimethyldimethoxysilane, 0.17 g of titanium (IV) butoxide, 1.67 g sodium methoxide (25% solution in methanol), 850 g toluene, 450 g water, and 450 g methanol. The contents of the flask were heated to reflux for 2 hours. The contents of the flask were then cooled to about 60° C., after which a dean-stark trap was applied. Heating of the flask was continued to collect the volatile materials from the flask until the temperature reached about 76° C. The bottom phase was collected until the temperature of the flask reaches about 112° C. The flask was heated at about 112° C. for 30 minutes, and the dean stark trap was opened to allow all volatiles to be distilled. The contents of the flask were heated to 130° C. under stirring for two hours. The contents of the flask were cooled to 50° C., and 5 g of silica-alumina catalyst support (grade 135) are disposed in the flask, following by stirring for 10 minutes. 300 g of toluene were disposed in the flask, followed by 10 g of activated carbon, and the contents of the flask were stirred overnight at room temperature. The contents of the flask were then filtered over a 0.45 micron PTFE filter membrane to provide 1482 g of a clear liquid, which included a cationic polymerizable material comprising a silicone resin. A sample of the clear liquid was heated at 150° C. for 2 hours to determine non-volatile content, which was 70.5%. The clear liquid was concentrated to a silicone resin solution having a non-volatile content of 87.9% by rotary evaporation.

Preparation Example 2

A cationic polymerizable material was prepared. In particular, a 5 L round bottom flask equipped was loaded with 437.7 g of phenylmethyldimethoxysilane, 55.5 g of bis(dimethylvinyl)disiloxane, 374.2 g of isobutyltrimethoxysilane, and 1000 g of toluene. 22.9 g of trifluoromethanesulfonic acid (5% in water) was then slowly disposed in the flask. Water was added to the flask at a rate of 31.1 g/min for 15 min to control the exothermic nature of the hydrolysis reaction within the flask. The flask temperature was maintained below 40° C. during the addition of water. A diphasic solution resulted. The diphasic solution was heated to reflux for 2 hours. After 2 hours, the flask was cooled to 50° C., and the acid was neutralized with 7.5 g potassium hydroxide (30% in water). 222.18 g of trimethoxy[2-(7-oxabicyclo[4.1.0]hept-3-yl)ethyl]silane was disposed in the flask and the contents of the flask were again heated to reflux for 2 hours. The contents of the flask were then azeotropically distilled to dryness and held at 130° C. for 15 hours. The contents of the flask were cooled to 75° C., and 4.8 g of silica-alumina catalyst support (grade 135) and 4.5 g of activated carbon were disposed in the flask. 200 g of toluene was disposed in the flask. The contents of the flask were then filtered over a 0.45 micron PTFE filter membrane to provide a clear liquid, which included a cationic polymerizable material comprising a silicone resin. The clear liquid was concentrated to a silicone resin solution having a non-volatile content of 85% by rotary evaporation.

Preparation Example 3

A silane compound was prepared. In particular, 512.8 g of triethylsilane was added dropwise to a solution of vinylcyclohexenemonoxide (668.1 g) and Rh(PPh$_3$)$_3$Cl (42 mg) under stirring at 95° C. Upon addition of the triethylsilane, the exothermic reaction increased temperature to about 105° C. The mixture was stirred for 12 hours at 95° C. to form a reaction mixture, which was twice distilled in an 18" jacketed distillation column. The resulting silane compound had a viscosity of about 7 cP at 25° C.

Preparation Example 4

A silane compound was prepared. In particular, a solution of N-heterocyclic carbine platinum catalyst in vinylcyclohexenemonoxide (472 g) was heated to 70° C., and phenyldimethylsilane (461 g) was added dropwise over 2 hours to the mixture keeping the temperature below 90° C. The crude mixture was then distilled under vacuum (4 torr) to give 839 g (95%) of a clear liquid product identified as [2-(3-{7-oxabicyclo[4.1.01 heptyl})ethyl][phenyl]dimethylsilane. The resulting silane compound had a viscosity of about 25 cP at 25° C.

Practical Example 1

50 g of the cationic polymerizable material of Preparation Example 1 were warmed to 60° C. The cationic polymerizable material was combined with 15.37 g of the silane compound of Preparation Example 3 and 1.31 g of a catalyst. The cationic polymerizable material, the silane compound, and the catalyst were mixed by shaking to form a curable composition, which was stored in a freezer at −15° C. until its use.

Practical Example 2

50 g of the cationic polymerizable material of Preparation Example 2 were combined with 15.9 g of the silane compound of Preparation Example 3 and 2.65 g of 1,4-cyclohexenedimethanol diglycidyl ether to form a mixture. The mixture was blended and shaken. 1.46 of a catalyst (the same as Practical Example 1) was added to the mixture, which was again shaken to form a curable composition, which was stored in a freezer at −15° C. until its use.

Practical Example 3

369 g of the silane compound of Preparation Example 4 was mixed with a 72% solution of phenyl- and epoxy-functional silsesquioxane in toluene, and the solvent was evaporated on a rotary evaporator. An iodonium/isothioxanthone photoacid generator was added and the product was filtered. This liquid filtered product was selectively cured using UV radiation to give patterned structures.

Application Example 1

A polyimide film (commercially available under the tradename Kapton® MT from DuPont of Wilmington, Del.) was adhered to a 6" silicon wafer to form a substrate. The substrate was cleaned with an IPA cleanroom wipe and toluene was spin coated thereon for 30 seconds at 1000 rpm. A thin film of primer was applied on the substrate, which was allowed to stand under ambient conditions for 30 minutes. The primer comprised a blend of toluene and butanone and is commercially available under the tradename PR-1205 from Dow Corning Corporation of Midland, Mich. The curable composition of Practical Example 1 was poured onto the primed substrate and spin coated at 200 RPM to form a film. The film was baked on a hotplate at 110° C. for two minutes and cooled to room temperature. The film was cured via irradiation from a mercury arc lamp (strongest emission line at 365 nm) with a 1.2 J/cm2 dosage, after which the film was again baked at 110° C. The spin coating and cure process was repeated once more, after which the resulting film was baked at 130° C. for 30 minutes to prepare a cured product formed from the curable composition. The cured product had excellent physical properties, including resistance to curling, flexibility, and adhesion to the substrate.

Application Example 2

The procedure of Application Example 1 was repeated, except the curable composition of Practical Example 2 was utilized in place of the curable composition of Practical Example 1. The cured product had excellent physical properties, including resistance to curling, flexibility, and adhesion to the substrate.

Comparative Example 1

The procedure of Application 1 was repeated, except the silane compound of Preparation Example 3 was not included. Said differently, the curable composition of Comparative Example 1 merely included the cationic polymerizable material of Preparation Example 1 and the catalyst. The cured product separated from the substrate and curled significantly such that opposite edges of the cured product contacted one another as they curled inwards.

The invention has been described in an illustrative manner, and it is to be understood that the terminology which has been used is intended to be in the nature of words of description rather than of limitation. Obviously, many modifications and variations of the present invention are possible in light of the above teachings. The invention may be practiced otherwise than as specifically described. Calling an example a comparative example does not mean that it is prior art.

What is claimed is:

1. A curable composition, comprising:
   a cationic polymerizable material comprising an organopolysiloxane resin represented by the following siloxane unit formula:

where $R^1$-$R^6$ are independently selected from a substituted or unsubstituted hydrocarbyl group or cationic polymerizable group;
   a+b+c+d=1; wherein 0≤a<0.4; 0<b<1; 0<c<1; 0≤d<0.4; and 0.01≤b/c≤0.3; and
   a, b, c and d designate an average mole number of each siloxane unit in one mole of the organopolysiloxane resin; and
      a diluent component comprising a silane compound having a single, and no more than a single, silicon-bonded cationic polymerizable group, wherein said silane compound is free from any silicon-bonded hydrolysable groups, in an amount sufficient to provide at least 15 percent by weight of the silane compound based on the total weight of the curable composition wherein said silane compound is free of siloxane bonds and has the following general formula:

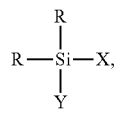

where R is an independently selected substituted or unsubstituted hydrocarbyl group, Y is said single silicon-bonded cationic polymerizable group, and X is selected from R and $SiR_3$.

2. The curable composition of claim 1 wherein said cationic polymerizable group of the organopolysiloxane resin and/or the silane compound is selected from a cyclic ether group, a cyclic ester group, a thietane group, a dioxepane group, acyclic carbonate group, a vinyl ether group, a divinyl ether group, a vinyl ester group, a diene group, a tertiary vinyl group, a styrene group, and a styrene derivative group.

3. The curable composition of claim 1 wherein said silane compound has a viscosity of less than 1,000 cP at 25° C.

4. The curable composition of claim 1 wherein said diluent component further comprises a cationic polymerizable compound other than said silane compound.

5. The curable composition of claim 1 further comprising a catalyst.

6. A method of preparing a cured article, said method comprising:
   applying the curable composition of claim 1 on a substrate to form a film; and
   curing the film on the substrate to form the cured article.

7. The method of claim 6 wherein the substrate comprises a flexible polymeric substrate.

8. The method of claim 6 wherein curing the film comprises exposing the film to radiation at a dosage sufficient to cure the film.

9. The method of claim 6 wherein curing the film comprises exposing at least one portion of the film to radiation at a dosage sufficient to cure the at least one portion of the film.

10. A cured article formed in accordance with the method of claim 6.

11. A waveguide comprising a cured article formed in accordance with the method of claim 6.

* * * * *